US 6,528,076 B2

(12) United States Patent
Small

(10) Patent No.: US 6,528,076 B2
(45) Date of Patent: Mar. 4, 2003

(54) TOPICAL COMPOSITIONS AND METHODS FOR TREATING PAIN

(75) Inventor: Robert Small, New York, NY (US)

(73) Assignee: Magic Herb Corp., New York, NY (US)

( * ) Notice: Subject to any disclaimer, the term of this patent is extended or adjusted under 35 U.S.C. 154(b) by 17 days.

(21) Appl. No.: 09/919,146

(22) Filed: Jul. 31, 2001

(65) Prior Publication Data

US 2003/0012830 A1 Jan. 16, 2003

Related U.S. Application Data

(60) Provisional application No. 60/303,671, filed on Jul. 6, 2001.

(51) Int. Cl.[7] .................................................. A61K 7/00
(52) U.S. Cl. ....................................................... 424/401
(58) Field of Search ........................... 424/401; 514/825

(56) References Cited

U.S. PATENT DOCUMENTS

| | | | |
|---|---|---|---|
| 4,808,576 A | 2/1989 | Schultz et al. | |
| 5,124,320 A | 6/1992 | Ivy et al. | |
| 5,223,257 A | * 6/1993 | Arora | 424/742 |
| 5,223,267 A | * 6/1993 | Nichols | 424/400 |
| 5,589,180 A | 12/1996 | Hind | |
| 5,601,838 A | 2/1997 | Hind | |
| 5,612,382 A | 3/1997 | Fike | |
| 5,637,314 A | 6/1997 | Sharpe et al. | |
| 5,650,157 A | 7/1997 | Bockow | |
| 5,667,799 A | 9/1997 | Caldwell et al. | |
| 5,698,206 A | 12/1997 | Becker et al. | |
| 5,736,126 A | 4/1998 | Van Engelen et al. | |
| 5,741,510 A | 4/1998 | Rolf et al. | |
| 5,753,266 A | 5/1998 | Youssefyeh et al. | |
| 5,753,270 A | * 5/1998 | Beauchamp et al. | 424/667 |
| 5,804,568 A | 9/1998 | Rubinfeld | |
| 5,807,568 A | 9/1998 | Cody et al. | |
| 5,843,467 A | 12/1998 | Ambroziewigz | |
| 5,853,768 A | 12/1998 | Altadonna | |
| 6,060,062 A | 5/2000 | Fowler | |
| 6,143,303 A | 11/2000 | Janakiram et al. | |
| 6,146,324 A | 11/2000 | Engel | |
| 6,211,250 B1 | 4/2001 | Tomlinson et al. | |
| 6,217,914 B1 | 4/2001 | Meisner | |
| 6,218,374 B1 | 4/2001 | Rubinfeld | |
| 6,235,314 B1 | 5/2001 | Niazi | |
| 6,245,348 B1 | 6/2001 | Williiams | |
| 6,245,802 B1 | 6/2001 | Iyengar et al. | |
| 6,248,731 B1 | 6/2001 | Blahut | |
| 6,248,763 B1 | 6/2001 | Scivoletto | |

* cited by examiner

Primary Examiner—Jose' G. Dees
Assistant Examiner—Konata M. George
(74) Attorney, Agent, or Firm—Coudert Brothers LLP

(57) ABSTRACT

Disclosed herein are topical compositions and methods for using the same to relieve pain in humans, such as pain associated with cancer, bone injuries, old age, and many other forms of pain. Specifically, the present compositions comprise an effective amount of acetone, a salicylate-based compound and an emollient. In addition, the present compositions further comprise one or more compounds including, but not limited to, terpenes and essential oils. The present compositions may be in the form of a liquid (preferably a slightly viscous liquid) or other forms including, but not limited to, salves, creams, gels, ointments or sprays.

76 Claims, No Drawings

TOPICAL COMPOSITIONS AND METHODS FOR TREATING PAIN

I. CROSS REFERENCE

This application claims priority of Provisional Application Ser. No. 60/303,671, filed Jul. 6, 2001.

II. FIELD OF THE INVENTION

The present invention is directed to a topical composition for treating pain in mammals. Specifically, the present invention comprises a safe and effective amount of acetone, a salicylate-based compound, an emollient and one or more compounds which can function as an analgesic and/or skin penetration enhancer, such as terpenes and essential oils.

The present invention is also directed to methods for treating pain and for topically applying an effective amount of the present composition to the area of pain.

III. BACKGROUND

An area of on-going research is the development of safer and effective methods for reducing or eliminating pain using transdermal analgesic formulations. Over time, a variety of such analgesic formulations have been developed. These include lotions and ointments containing aspirin or any of a number of non-steroidal anti-inflammatory agents. While many of the currently available analgesic formulations reduce pain to some degree, there is, nonetheless, a continued interest in identifying new formulations which provide longer lasting pain relief in a short period of time.

It is therefore an object of the present invention to provide a safe topical composition that provides effective pain relief in a sufficiently short period of time. Further objects of the present invention will be apparent from the descriptions herein.

IV. SUMMARY OF THE INVENTION

The present invention provides a composition comprising acetone, a salicylate-based compound, an emollient and one or more terpenes and essential oils. The present invention is also directed to methods for treating pain and for topically applying an effective amount of the present compositions to the area of pain.

V. DETAILED DESCRIPTION OF THE INVENTION

A. Compounds Utilized in the Present Composition

The composition of the present invention comprises acetone, a salicylate-based compound and an emollient. Preferably, the present composition comprises commercial grade acetone, substantially free of impurities, including, but not limited to, water, benzene or phenol. More preferably, the acetone is at least 95% pure and/or contains less than 1% water, less than 100 ppm phenol and less than 100 ppm benzene, and most preferably less than 50 ppm phenol and 1 ppm benzene. Ideally, the acetone is phenol and benzene free.

The salicylate-based compounds used herein include, but are not limited to, salicylic acid, or derivatives thereof, such as methyl salicylate, sodium salicylate, acetyl salicylic acid, aloxipirin, calcium carbaspirin, choline salicylate, salicoside, salicylamide, acetylsalicylic acid, salicylsufuric acid, o-hydroxybenzoic acid, methyl ester, synthetic wintergreen oil, Betula oil, and salicylic acid. Other salicylate-based compounds which may be useful in the present invention are disclosed in U.S. Pat. No. 4,275,059 to Flora, which is incorporated herein by reference. Preferably, the salicylate-based compound is commercial grade, and more preferably the compound is greater than 95% pure and more preferably greater than 99% pure. The preferred salicylate-based compound is methyl salicylate, preferably having a purity ranging between 95% and 99.9%.

The present compositions may also include terpenes and essential oils. Examples of such compounds include, but are not limited to, alpha-terpinene, gamma terpinene, linalool, camphene, limonene, menthol, sabinene, menthene, alpha-phellandrene, alpha-pinene and beta-pinene, myrcene, isopulegol, 1,8-cineole (Eucalyptol), and the like. Preferably, these compounds are commercial grade, more preferably greater than 80% pure, and most preferably between 90 and 99.9% pure. Ideally, such compounds are between 97% and 99.9% pure. Other terpenes and essential oils which may be included in the present invention include, but are not limited to, junipene, camphor, mint oils, lidocaine, peppermint oil and eucalyptus oil. Preferably, these compounds are commercial grade and more preferably greater than 80% pure.

Emollients for use in the present compositions include, but are not limited to, the following:

1. Triglyceride esters which include, but are not limited to, vegetable and animal fats and oils such as palm oil, castor oil, cocoa butter, safflower oil, cottonseed oil, corn oil, olive oil, cod liver oil, almond oil, avocado oil, palm oil, sesame oil, squalene, kikui oil and soybean oil;
2. Acetoglyceride esters, including but not limited to acetylated monoglycerides;
3. Ethoxylated glycerides such as ethoxylated glyceryl monostearate;
4. Alkyl esters of fatty acids having 10 to 20 carbon atoms which include, but are not limited to, methyl, isopropyl and butyl esters of fatty acids;
5. Alkenyl esters of fatty acids having 10 to 20 carbon atoms such as oleyl myristate, oleyl stearate, and oleyl oleate;
6. Fatty acids having 10 to 20 carbon atoms such as pelargonic, lauric, myristic, palmitic, stearic, isostearic, hydroxystearic, oleic, linoleic, ricinoleic, arachidic, behenic, and erucic acids;
7. Fatty alcohols having 10 to 20 carbon atoms such as lauryl, myristyl, cetyl, hexadecyl, stearyl, isostearyl, hydroxystearyl, oleyl, ricinoleyl, behenyl, erucyl, and 2-octyl dodecanyl alcohols;
8. Lanolin and lanolin derivatives including, but not limited to lanolin, lanolin oil, lanolin wax, lanolin alcohols, lanolin fatty acids, isopropyl lanolate, ethoxylated cholesterol and lanolin alcohols;
9. Polyhydric alcohol esters, including but not limited to, ethylene glycol mono and di-fatty acid esters, diethylene glycol mono-and di-fatty acid esters and polyethylene glycol (200–6000) mono- and di-fatty acid esters;
10. Wax esters such as beeswax, spermaceti, myristyl myristate, stearyl stearate;
11. Beeswax derivatives including but not limited to, polyoxyethylene sorbitol beeswax;
12. Vegetable waxes including, but not limited to, carnauba and candelilla waxes;
13. Phospholipids such as lecithin and derivatives;

14. Sterols including, but not limited to, cholesterol and cholesterol fatty acid esters; and
15. Amides such as fatty acid amides, ethoxylated fatty acid amides, and solid fatty acid alkanolamides.

Preferably, the emollient utilized in the present invention is commercial grade. The preferred emollient of the present invention is palm oil. Skin-conditioning compounds which may also be included in the present invention are disclosed in U.S. Pat. No. 6,174,533 to Sanogueira, Jr., which is incorporated herein by reference.

The following descriptions represent various embodiments of the present compositions. These embodiments are not intended to limit the scope of the invention. The amount of each ingredient in the composition is given in weight percent based on the total weight of the composition. Such ingredients can be synthetically prepared and/or derived from natural sources. Further, the compositions of the present invention may comprise, consist of or consist essentially of the ingredient's identified herein. Embodiments disclosed herein can be formulated by combining, adding, mixing and/or blending the herein described ingredients (e.g., in commercial grade form) using standard techniques known in the art.

The topical composition of the present invention generally comprises from about 1% to about 70% of the salicylate-based compound, about 1% to about 70% acetone and about 1% to about 30% of an emollient.

A preferred composition generally comprises from about 5% to about 60% of the salicylate-based compound, preferably from about 5% to about 30%, more preferably from about 5% to about 20%, and most preferably about 8.6%. The present compositions may also comprise from about 1% to about 7% of the salicylate-based compound, or about 10% to about 40%, or about 55% to about 70%, or about 10% to about 70%. Many patients are in the habit of taking analgesics for prolonged periods and usually in excessive doses. Thus, the preferred ranges are more appropriate to avoid analgesic overuse noted in patients.

Another preferred composition of the present invention generally comprises from about 10% to about 70% acetone, preferably from about 15% to about 60%, more preferably from about 15% to about 35%, and most preferably about 25%. The present compositions may also comprise about 10% to about 24% acetone, or about 26% to about 70%, or about 30% to about 70%.

Another preferred composition of the present invention comprises from about 5% to about 20% of an emollient, preferably from about 5% to about 15%, more preferably from about 1% to about 5%, and most preferably about 3%. The present compositions may also comprise about 4% to about 20% of an emollient or about 8% to about 20%.

Another preferred composition of the present invention comprises about 1% to 60% menthol, preferably about 10% to 50%, more preferably about 20% to 40%, and most preferably about 33%. The present composition may also comprise about 1% to about 9% menthol, about 11% to about 30%, about 35% to about 60%, or about 1% to about 30%.

In the composition of the present invention water, camphene, gamma-terpinene, myrcene, menthene, alpha-phellandrene, linalool, isopulegol, junipene and alpha-terpinene are most preferably present in the following approximate amounts: 0.5%, 0.3%, 0.3%, 0.4%, 0.04%, 0.05%, 0.02%, 0.09%, and 0.13%, respectively.

In an alternative embodiment, the present composition may also include zero to about 5% of the following ingredients i) sabinene; (ii) myrcene; (iii) menthene; (iv) alpha-phellandrene; (v) linalool; (vi) isopulegol; (vii) junipene; (viii) alpha-terpinene; (ix) gamma-terpinene; and (x) water. The present composition may also comprise the above ingredients in amounts ranging between about 0.01% to about 5%, about 0.01% to about 1%, or about 0.2% to about 2%.

Another preferred composition of the present invention may comprise about 1% to about 30% alpha-pinene, preferably about 10% to about 20%, more preferably about 12% to about 16%, and most preferably about 14.5%. The present compositions may also comprise about 1% to about 13% alpha-pinene, or about 20% to about 30%.

Another preferred composition of the present invention may comprise about 0.1% to about 5% beta-pinene, limonene or sabine, preferably about 0.1% to about 5%, more preferably about 1% to 2%, and most preferably 1.7%, 1.8% and 1.54% respectively of each compound. The present compositions may also comprise about 0.1% to about 1% and about 3% to about 5% of beta-pinene, limonene or sabine.

Another preferred composition of the present invention may comprise about 1% to about 20% Eucalyptol, preferably about 1% to about 10%, more preferably about 3% to about 7%, and most preferably about 5.6%. The present composition may also comprise about 1% to about 4% Eucalyptol, or about 7% to about 10%, or about 13% to about 10%.

Another preferred composition of the present invention comprises the following ingredients in a slightly viscous liquid form:

TABLE 1

| INGREDIENT | APPROXIMATE PURITY | APPROXIMATE AMOUNT (w/w) |
| --- | --- | --- |
| Water | | 0% to 5% |
| Acetone | >98% | 15% to 35% |
| Menthol | >90% | 15% to 40% |
| Palm Oil | >95% | .5% to 10% |
| 2,6,6,-Trimethyl Bicyclo-(3,1,1)-2-Heptene (alpha-pinene) | >96% | 1% to 30% |
| Bicyclo[2.2.1]heptane, 2,2-dimethy 1-3-methylene (camphene) | >97% | 0% to 5% |
| Bicyclo[3.1.0]hexane, 4-methylene-1-(1-methyl) (sabinene) | >93% | 0% to 5% |
| Bicyclo[3.1.1]heptane, 6,6-dimethy-2-methylene (beta-pinene) | >96% | 0% to 5% |
| Limonene | >97% | 0% to 5% |
| 1,8-Cineole (Eucalyptol) | >93% | 1% to 20% |
| Benzoic acid, 2-hydroxy-, methyl ester (methyl salicylate) | >96% | 5% to 30% |
| 1,4-methanoazulene, decahydro-4,8,8-trimethyl-9 methylene (Junipene) | >98% | 0% to 5% |
| Myrcene | >95% | 0% to 5% |
| Menthene | >80% | 0% to 5% |
| alpha-Phellandrene | >92% | 0% to 5% |
| Linalool | >90% | 0% to 5% |
| Isopulegol | >92% | 0% to 5% |
| gamma-terpinene | >94% | 0% to 5% |
| alpha-terpinene | >97% | 0% to 5% |

If necessary, the amount of each ingredient in the present compositions may be modified to accommodate any special needs of a patient. Such modifications include reducing the amount of acetone, salicylate based compound or emollient to an appropriate, yet effective dosage. These modifications may also include eliminating or reducing the amount of certain terpenes and essential oils, including, but not limited to, camphene, alpha-terpenes, myrcene, methane, alpha-phellandrene, linalool, isopulegol, junipene and gamma-terpinene. Specifically, such modified formulations may include, but are not limited to the following:

TABLE 2

| Ingredients | Approximate Percentage (% w/w) |
|---|---|
| Acetone | 15% to 35% |
| Emollient | 0.5% to 10% |
| alpha-pinene | 1% to 3% |
| beta-pinene | 0.1% to 5% |
| Limonene | 0.1% to 5% |
| Sabinene | 0.1% to 5% |
| Eucalyptol | 1% to 2% |
| Menthol | 15% to 40% |
| Methyl Salicylate | 5% to 30% |

TABLE 3

| Ingredients | Approximate Percentage (% w/w) |
|---|---|
| Acetone | 15% to 35% |
| Emollient | 0.5% to 10% |
| alpha-pinene | 1% to 30% |
| Eucalyptol | 1% to 20% |
| Menthol | 15% to 40% |
| Methyl Salicylate | 5% to 30% |

TABLE 4

| Ingredients | Approximate Percentage (% w/w) |
|---|---|
| Acetone | 15% to 35% |
| Emollient | 0.5% to 10% |
| alpha-pinene | 1% to 30% |
| Menthol | 15% to 40% |
| Methyl Salicylate | 5% to 30% |

The present compositions may be in the form of a liquid solution (preferably a slightly viscous liquid) or blended into a tissue compatible vehicle, such as a hydrophilic lotion, ointment, cream, salve, spray or gel using conventional methods known in the art. For example, gel based vehicles are well known in the art and commercially available for formulation with active ingredients to form a suitable topical application. Examples of such gel based vehicles may include, but are not limited to, the commercially available Dermabase and Unibase formulations. Also, when used in gel form, a gelling agent may be present in an amount sufficient to provide the appropriate viscosity, generally being up to about 30%, preferably from about 0.5% to 20%, more preferably from about 1% to 5%. Examples of suitable gelling agents may include, but are not limited to, carboxyl vinyl polymers, hydroxycellulose, hydroxyethyl cellulose, hydroxypropyl methyl cellulose, methyl cellulose and carboxyl methyl cellulose.

Ointments and creams containing the compositions of the present invention may be formulated using standard techniques known in the industry. For example, such formulations may be produced with an oily base with the addition of suitable thickening and/or gelling agents. Such bases may include water and/or an oil such as liquid paraffin or a vegetable oil such as peanut oil or castor oil. Thickening agents which may be used according to the characteristics of the base may include, for example, soft paraffin, aluminum stearate, cetostearyl alcohol, propylene glycol, polyethylene glycols, woolfat, hydrogenated lanolin, beeswax and the like.

The present compositions may also be formulated into lotions or salves using methods known in the art. For example, such lotions or salves may be formulated with an aqueous or oily base and will include also, in general, one or more of the following: stabilizing agents, emulsifying agents, dispersing agents, suspending agents, thickening agents, coloring agents, perfumes, and the like.

The present compositions may also be in the form of an aerosol using methods known in the art. For example, aerosol formulations for use with the present composition would typically include propellants, surfactants and co-solvents and may be filled into conventional aerosol containers that are closed by a suitable metering valve.

B. Method of Applying the Present Compositions to Treat Pain

A pain treatment application using the topical compositions of the present invention may employ one or more of the following steps:

1) applying an effective amount of the present composition on the exact location or area around the location of pain;

2) massaging the present composition on the skin using moderate pressure until the moist sensation between the applicant's hand and patient's skin disappears; and 3) reapplying the present composition multiple times in the manner described above for approximately 6 to 10 minutes, or until the pain subsides, preferably for no more than 20 minutes.

An "effective amount" includes an amount of the present composition sufficient to cover the exact region or at least a majority of the region of skin overlying the pain. A patient may receive up to five treatment applications (or more) each day until the pain subsides.

Other method steps of applying the present formulation to an area of pain include, but are not limited to, the following.

Hot Bath 1) diluting one part of the composition to five parts hot water in a bath; and 2) soaking a pain affected area in the bath for approximately 10 to 20 minutes, or until the pain subsides.

Hot Compress 1) providing the present composition in a hot compress;

2) applying the hot compress to the area of pain;

3) applying moderate pressure to the hot compress while it is placed on the area of pain; and 4) reapplying the hot compress multiple times in the manner described above for 5 to 10 minutes, or until the pain subsides.

Whirlpool Bath 1) diluting one part of the composition to five parts hot water in a whirlpool bath; and 2) soaking a pain affected area in the bath for about 10 to 20 minutes, or until the pain subsides, such that the motion of the water facilitates the penetration of the present composition through the patient's skin.

C. Methods of Using the Present Compositions to Treat Pain

The present compositions may be used to treat pain associated with many conditions by topically applying the compositions to the area of pain as described above. Specifically, the compositions herein may be used to treat pain, including, but not limited to, arthritis, pain associated with cancer, neck pain, shoulder pain, back pain, surgical pain, preoperative and postoperative pain, temporal mandibular joint syndrome, carpal tunnel syndrome, and bone injury pain.

The compositions herein may also be used to treat pain associated with osteoarthritis, auto-immune diseases such as rheumatoid arthritis and psoriatic arthritis, gout, psuedo gout, ankylosing spondylitis, juvenile arthritis, systemic lupus erythematosus, arthritis associated with an infection, scleroderma and fibromyalgia.

In addition, the compositions herein may be used to treat muscle pain, pain associated with muscle tension, fatigue, curvature of the spine, minor and major spinal disc compression, pinched nerves, strained or sprained muscles, and nervous tension.

Moreover, the present compositions may be used to treat pain associated with traumatic injuries, hematomas, myositis, lower back syndromes, spinal stenosis, joint pain, bone pain and bone fractures caused by metastic cancer, such as breast, lung, or prostrate cancer. Other cancers that can cause such pain include sarcomas and osteosarcomas. The present composition may also be used to treat muscle, bone and joint pain generally associated with cancer.

The present compositions may be used to treat pain associated with osteoprotic fractures of the lumbar spine and other sites, and traumatic bone fractures, including pelvic fractures. With respect to joint pain, the compositions herein may be used to decrease overall joint stiffness and increase joint mobility.

The present compositions may also be used to treat pain associated with pre-surgical and post-surgical orthopedic procedures. For example, the present compositions may be applied to treat such pain before or after arthroscopy, especially in the shoulders or knees.

In addition, the present compositions may be used for treating pain associated with post-surgical orthopedic recovery, such as tendon, muscle and bone repair, as well as joint replacement, including hip or knee replacement. For example, bone fractures require the use of plates, screws or other attachment means to hold the bones together. Placement of these devices requires surgery, and the post-surgical pain resulting therefrom can be treated with the present compositions.

Further, the compositions herein may be used to treat pain caused by herniated nucleus pulposus (slipped disc), musculo-skeletal pain, joint dislocations, herniated intervetebral disc, prolapsed intervetebral disc (including lumbar and cervical), ruptured disc, whiplash injuries, fibromyositis, intercostal rib pain, muscle tear, tendonitis, bursitis, meniscal tears, tendon tears, and bone spurs. The compositions herein may also be used to treat pain such as cervical muscle hyperactivity (spasm), an extremely common condition with many causes, including tension, response to an inflamed or subluxed joint, arthritic changes, poor posture or work habits, trauma, systemic disease and adjacent pathology.

The compositions of the present invention may be used to treat pain caused by sports related injuries. Such sports-related injuries include, but are not limited to, hematomas, bruises, sprains (e.g., ankle sprain), muscle spasms (e.g., pulled muscles), partial tendon tears, tendonitis, bursitis, myositis, traumatic arthritis and post-insertion of joint dislocation. In treating pain associated with sports related injuries, the present compositions would be applied to the area of pain as described herein. The present compositions may be used in combination with sports-injury therapy techniques such as physical therapy, acupuncture, weight-training, biofeedback techniques, among others.

The present compositions may also be used in treating pain unique to senior citizens. Much of the bone, joint or muscle pain experienced by seniors results from a combination of sources. Some of these sources are known, others are not. In certain cases, such pain is a natural consequence of the diseases resulting from the aging process, which includes pain accompanied with diminished motor function, atrophy, dietary changes, among others. Consequently, pain management in seniors is difficult. Often times, seniors are required to take multiple medications daily in order to effectively manage their pain. This poses significant drawbacks to seniors, such as side effects from the medications, adverse reactions in mixing the medications, as well as excessive costs and effort to maintain the required medication regimen on a daily basis.

Thus, using the present compositions to treat bone, joint or muscle pain in seniors can be effective in minimizing the amount of pain relief medication they already take, or would be required to take in the future. Also, pain in seniors contributes to depression, inactivity and immobility in this age group. Diminution in pain resulting from use of the present compositions would result in greater independence, increased activity, socialization, appetite and overall sense of well-being in an elderly patient.

In addition, the compositions of the present invention can be utilized as an adjunct to physical therapy. Generally, physical therapy involves passive and active treatments or methodologies to strengthen and/or heal muscles, tendons, bones, and joints. The draw backs of physical therapy include pain and discomfort to the patient. The formulations of the present invention can be used to treat such pain. For example, the present formulation may be applied to the area of pain (as described herein) before, during, and/or after each physical therapy treatment.

The present compositions can also be used to treat pain associated with immobilized tissue. Treatment of damaged muscles, bones, tendons, and joints often requires that tissues be immobilized for an extended period of time. In these circumstances, the tissue is kept immobilized by a variety of devices including, but not limited to, braces, slings, casts, bandages and splints. Oftentimes, when the device is removed and continuing thereafter, the patient experiences muscle, bone, tendon and/or joint pain in or about the immobilized area. The present formulation can be used to treat such pain by applying the formulation to the area of pain in the manner described herein.

TENS or transcutaneous electro-nerve stimulation is characterized by high voltage, sensory current and is used to block pain. The present compositions can be used in conjunction with electrical neuromuscular stimulation to increase the effectiveness of the pain treatment. For example, before or after treatment with electrical neuromuscular stimulation, the present composition can be applied to the affected area in the manner described herein.

The present composition can also be used in combination with local or other injections of an anesthetic, such as lidocane (with and without steroids). For example, a needle containing lidocane (with or without a steroids) can be injected into the skin overlying the area of pain. This area of the skin can be further anesthetized by applying the present composition at or around the injection site before or after the injection.

In addition, the present composition may be used in combination with oral analgesics or anti-inflammatories (e.g., NSAIDS and Cox-2-inhibitors) to alleviate pain. When used in such manner, for example, the composition herein can provide an enhanced and/or additive pain relief effect.

The present composition may also be used in combination with heat treatment devices including, but not limited to, hot packs such as heating pads or hot towels. Such devices may also include Diathermy which is a deep tissue heat treatment, wherein the temperature of the injured tissues is raised by high frequency current, ultrasonic waves, or microwaves radiation. Diathermy is used to reduce pain, relieve muscle spasm, decrease soft-tissue contractures, resolve inflammation, and promote healing. The present compositions can be used in combination with hot packs or Diathermy to provide an enhanced and/or additive relief effect.

Further, the present composition may be used in combination with morphine-like agents, such as codeine, opiates, oxy-cotcontin, Percocet, Demorol, and Vicadin. When used in such manner, for example, the morphine-like agents, together with any of the formulations of the present invention, can achieve an analgesic effect that would otherwise require a higher dosage of opioids but with fewer side effects.

In addition, the present composition may be used in combination with biofeedback techniques. Biofeedback is a useful technique for achieving stress reduction, reducing anxiety and alleviating psychosomatic symptoms by monitoring and controlling certain physiological processes. The use of biofeedback techniques in combination with the compositions herein may allow the patient to achieve greater control over his or her physiological processes and to achieve greater reduction in pain than through the use of such techniques.

The present compositions can also be used in combination with acupuncture therapy. Acupuncture therapy generally involves inserting tiny needles at certain specific points on the surface of the body. Acupuncture has proven efficacy in relieving pain. Acupuncture may also be useful for the treatment of osteoarthritis, low back pain, carpal tunnel syndrome, fibromyalgia, and other conditions that cause chronic pain. The compositions herein may provide an enhanced and/or additive relief effect when used in combination with acupuncture.

Pain associated with cancer is one of the most severe forms of pain. Such pain can be further exacerbated by cancer treatments, including radiation therapy and chemotherapy. The present compositions may be used to treat cancer associated pain in muscles, bones, and joints. The present compositions can also be used in combination with currently available treatments for such pain to provide an enhanced and/or additive relief effect.

Utilizing the present compositions to reduce pain in cancer patients would bring about, for example, improved mood and motivation of the patient, as well as pain relief from the cancer itself and the pain brought about by the patient's continued cancer therapy treatments. Also, when treated in such a manner, the patient may experience improved mobility, thus increasing the patient's chances for successfully conducting daily activities and improving the patient's overall well being. By using the compositions herein, the patient may also experience greater flexibility in going to and from cancer treatment sessions.

The following examples are illustrative of the methods of treating humans with the compositions of the present invention. These examples are not intended to limit the scope of the present invention.

EXAMPLE 1

Treatment of Osteoarthritic Pain From Osteoarthritis

An osteoarthritic patient was treated with the formulation (in a slightly viscous liquid form) comprising the ingredients listed in Table 5 below.

TABLE 5

| Ingredients | Approximate Percentage (% w/w) |
| --- | --- |
| Water | 0.5% |
| Acetone | 25.0% |
| Palm Oil | 3.0% |
| alpha-pinene | 14.5% |
| beta-pinene | 1.7% |
| Camphene | 0.3% |
| gamma-Terpinene | 0.3% |
| Limonene | 1.8% |
| Sabinene | 1.54% |
| Myrcene | 0.4% |
| Menthene | 0.04% |
| alpha-phellandrene | 0.05% |
| Linalool | 0.02% |
| Isopulegol | 0.09% |
| Junipene | 0.09% |
| alpha-terpinene | 0.13% |
| Eucalyptol | 5.6 |
| Menthol | 33.0 |
| Methyl Salicylate | 8.6 |

The composition described in Table 5 was applied directly on the skin over the entire location of the pain. The patient was positioned (e.g., in a supine or leaning position) such that application of the composition would occur most effectively. Using a disposable glove, the composition was applied using moderate pressure in a massage fashion until the moist sensation between the gloved hand and patient's skin disappeared. For each application, the composition was reapplied approximately 10 to 20 times using this procedure. Each application lasted between 6 and 10 minutes. The patient experienced a significant reduction in pain.

EXAMPLE 2

Treatment of Pain Associated with Bone Fractures Caused by Metastic Cancer

The composition described in Table 5 was used to treat pain associated with bone fractures caused by metastic cancer. For example, the present composition was applied directly on the skin over the entire location of the pain as described by a patient. The patient was positioned (e.g., in a supine or leaning position) such that application of the composition would occur most effectively. Using a disposable glove, the composition was applied using moderate pressure in a massage fashion until the moist sensation between the gloved hand and patient's skin disappeared. For each application, the composition was reapplied approximately 10 to 20 times using this procedure. Each application lasted between 6 and 10 minutes. In this study, the patient experienced a 50% immediate relief of pain.

EXAMPLE 3

Treatment of Pain Associated with Traumatic Injuries and Hematomas

Patients were treated for pain associated with traumatic injuries, including closed chest injuries, injuries to arms, legs and buttocks. Traumatic injuries result from a force applied to a body part of such intensity that causes pain and swelling. In the patients treated with the composition herein, the pain was present for at least 48 hours or more. The composition described in Table 5 was applied directly on the skin over the entire location of the pain as described by each of the patients. Each patient was positioned (e.g., in a supine or leaning position) such that application of the composition would occur most effectively. Using a disposable glove, the composition was applied using moderate pressure in a massage fashion until the moist sensation between gloved hand and patient's skin disappeared. For each application, the composition was reapplied approximately 10 to 20 times using this procedure. Each application lasted between 6 and 10 minutes. In this study, the majority of patients experienced a 75% to 100% immediate reduction in pain.

EXAMPLE 4

Treatment of Pain Associated with Meniscal Tears and Tendon Tears

Patients were treated for pain associated with meniscal and tendon tears. In these cases, the composition described in Table 5 was applied directly on the skin over the entire location of the pain as described by each patient. Each patient was positioned (e.g., in a supine or leaning position) such that application of the composition would occur most effectively. Using a disposable glove, the composition was applied using moderate pressure in a massage fashion until the moist sensation between the gloved hand and patient's skin disappeared. For each application, the composition was reapplied approximately 10 to 20 times using this procedure. Each application lasted between 6 and 10 minutes. Additional applications were made when the area of pain could not be treated by one application due to location, e.g., the composition was applied to both the front and back of the knee if the patient had knee pain. In this study, the majority of patients experienced from about 75% to 100% immediate relief of pain.

EXAMPLE 5

Treatment of Pain Associated with Rheumatoid Arthritis

Patients were treated for pain associated with Rheumatoid arthritis in the finger or knees. In these case, the composition described in Table 5 was applied directly on the skin over the entire location of the pain as described by each patient. Each patient was positioned (e.g., in a supine or leaning position) such that application of the composition would occur most effectively. Using a disposable glove, the composition was applied using moderate pressure in a massage fashion until the moist sensation between gloved hand and patient's skin disappeared. For each application, the composition was reapplied approximately 10 to 20 times using this procedure. Each application lasted between 6 and 10 minutes. Additional applications were made when the area of pain could not be treated by one application due to location. In this study, the patients experienced a greater than 75% immediate relief of pain.

EXAMPLE 6

Treatment of Pain Associated with Psoriatic Arthritis

The composition described in Table 5 was applied to treat pain associated with Psoriatic arthritis. The composition was applied directly on the skin over the entire location of the pain as described by the patient. The patient was positioned (e.g., in a supine or leaning position) such that application of the composition would occur most effectively. Using a disposable glove, the composition was applied using moderate pressure in a massage fashion until the moist sensation between gloved hand and patient's skin disappeared. For each application, the composition was reapplied approximately 10 to 20 times using this procedure. Each application lasted between 6 and 10 minutes. In this study, the patient immediately experienced greater than 75% pain relief.

EXAMPLE 7

Treatment of Pain Associated with Gouty Arthritis and Psuedo Gout

The composition described in Table 5 was used to treat pain associated with gout. The composition was applied directly on the skin over the entire location of the pain as described by the patient. The patient was positioned (e.g., in a supine or leaning position) such that application of the composition would occur most effectively. Using a disposable glove, the composition was applied using moderate pressure in a massage fashion until the moist sensation between gloved hand and patient's skin disappeared. For each application, the composition was reapplied approximately 10 to 20 times using this procedure. Each application lasted between 6 and 10 minutes. In this study, the patient experienced a greater than 75% immediate reduction in pain.

EXAMPLE 8

Treatment of Pain Associated with Myositis

Patients were treated for pain associated with myositis. In each of these patients, the composition described in Table 5 was applied directly on the skin over the entire location of the pain as described by each patient. Each patient was positioned (e.g., in a supine or leaning position) such that application of the composition would occur most effectively. Using a disposable glove, the composition was applied using moderate pressure in a massage fashion until the moist sensation between gloved hand and patient's skin disappeared. For each application, the composition was reapplied approximately 10 to 20 times using this procedure. Each application lasted between 6 and 10 minutes. Additional applications were made when the area of pain could not be treated by one application due to location. In this study, the majority of patients experienced from about 75% to 100% immediate relief of pain.

EXAMPLE 9

Treatment of Pain Associated with Tendonitis

Patients were treated for pain associated with tendonitis. In each of these patients, the composition described in Table 5 was applied directly on the skin over the entire location of the pain. Each patient was positioned (e.g., in a supine or leaning position) such that application of the composition would occur most effectively. Using a disposable glove, the composition was applied using moderate pressure in a massage fashion until the moist sensation between gloved hand and patient's skin disappeared. For each application, the composition was reapplied approximately 10 to 20 times using this procedure. Each application lasted between 6 and 10 minutes. Additional applications were made when the area of pain could not be treated by one application due to location. In this study, the patients experienced a greater than 75% immediate relief of pain.

EXAMPLE 10

Treatment of Pain Associated with Cervical Spasm

Patients were treated for pain associated with cervical spasm. In each of these patients, the composition described in Table 5 was applied directly on the skin over the entire location of the pain. Each patient was positioned (e.g., in a supine or leaning position) such that application of the composition would occur most effectively. Using a disposable glove, the composition was applied using moderate pressure in a massage fashion until the moist sensation between gloved hand and patient's skin disappeared. For each application, the composition was reapplied approximately 10 to 20 times using this procedure. Each application lasted between 6 and 10 minutes. Additional applications were made when the area of pain could not be treated by one application due to location, e.g., the composition was applied to both the front and back of the neck if the patient had neck pain. The majority of patients in this study experienced approximately 75% to 100% immediate pain relief.

EXAMPLE 11

Treatment of Pain Associated with Lower Back Syndromes

Patients were treated for pain associated with lower back syndromes. In each of these patients, the composition described in Table 5 was applied directly on the skin over the entire location of the pain. Each patient was positioned (e.g., in a supine or leaning position) such that application of the composition would occur most effectively. Using a disposable glove, the composition was applied using moderate pressure in a massage fashion until the moist sensation between gloved hand and patient's skin disappeared. For each application, the composition was reapplied approximately 10 to 20 times using this procedure. Each application lasted between 6 and 10 minutes. Additional applications were conducted where the area of pain could not be treated by one application due to location. The majority of patients in this study experienced approximately 75% to 100% immediate pain relief.

EXAMPLE 12

Treatment of Pain Associated with Herniated Discs

Patients were treated for pain associated with a herniated disc. In each of these patients, the composition described in Table 5 was applied directly on the skin over the entire location of the pain. Each patient was positioned (e.g., in a supine or leaning position) such that application of the composition would occur most effectively. Using a disposable glove, the composition was applied using moderate pressure in a massage fashion until the moist sensation between gloved hand and patient's skin disappeared. For each application, the composition was reapplied approximately 10 to 20 times using this procedure. Each application lasted between 6 and 10 minutes. The majority of patients in this study experienced approximately 75% to 100% immediate relief of pain.

EXAMPLE 13

Treatment of Pain Associated with Spinal Stenosis

Patients were treated for pain associated with spinal stenosis. In each of these patients, the composition described in Table 5 was applied directly on the skin over the entire location of the pain. Each patient was positioned (e.g., in a supine or leaning position) such that application of the composition would occur most effectively. Using a disposable glove, the composition was applied using moderate pressure in a massage fashion until the moist sensation between gloved hand and patient's skin disappeared. For each application, the composition was reapplied approximately 10 to 20 times using this procedure. Each application lasted between 6 and 10 minutes. In this study, the majority of patients experienced from about 75% to 100% immediate relief of pain.

EXAMPLE 14

Treatment of Pain Associated with Osteoprotic Fractures of the Lumbar Spine and Other Sites Patients were treated for pain associated with osteoprotic fractures of the lumbar spine and other sites. In each of these patients, the composition described in Table 5 was applied directly on the skin over the entire location of the pain as described by the patient. The patient was positioned (e.g., in a supine or leaning position) such that application of the composition would occur most effectively. Using a disposable glove, the composition was applied using moderate pressure in a massage fashion until the moist sensation between gloved hand and patient's skin disappeared. For each application, the composition was reapplied approximately 10 to 20 times using this procedure. Each application lasted between 6 and 10 minutes. In this study, the majority of patients immediately experienced from about 75% to 100% relief of pain.

EXAMPLE 15

Treatment of Pain Associated with Traumatic Bone Fractures, Including the Pelvis The composition described in Table 5 was used to treat pain associated with traumatic fractures including pelvic fractures. In one example, the present composition was applied directly on the skin over the entire location of the pain. The patient was positioned (e.g., in a supine or leaning position) such that application of the composition would occur most effectively. Using a disposable glove, the composition was applied using moderate pressure in a massage fashion until the moist sensation between gloved hand and patient's skin disappeared. For each application, the composition was reapplied approximately 10 to 20 times using this procedure. Each application lasted between 6 and 10 minutes. In this study, the majority of patients immediately experienced from about 75% to 100% relief of pain.

The results of the above trials showed some degree of pain relief in 83% of the 210 patients who participated in the study, or 175 people. Out of the 210 patients, 76%, or 160 persons, experienced approximately 75% to 100% pain relief. Another 7%, or 15 persons, experienced an approximate 10% to 50% pain relief. The remaining 17% of the patients, or 35 persons, experienced no pain relief. These results are summarized in Table 6.

TABLE 6

| Approximate Degree of Pain Relief (%) | Approximate Number of Persons | Approximate Percent of Total Population |
|---|---|---|
| 75–100 | 160 | 76% |
| 10–50 | 15 | 7% |
| 0 | 35 | 17% |

Of the 160 persons who experienced 75% to 100% pain relief, 12%, or 20 people, had complete relief of pain for at least three months. The remaining 88%, or 140 people, had near complete relief of pain that lasted for up to 4, 12 and 24 hours. Further, of the 83% of the patients, or 175 people, who experienced some degree of pain relief, such relief first occurred within a range of three minutes after initial application of the composition (and while the composition was still being applied) to up to 60 minutes after the application was completed.

When the composition was applied to the skin, approximately 60% of the patients expressed a warming sensation on the skin, and 15% expressed a cold sensation. Of the 75 patients who made return visits and had the composition reapplied at the same location or at different locations of pain, all experienced positive response to pain relief.

Based on the results found in this study, the present compositions are effective and competitive against other modalities of pain treatment including oral agents, physical therapy, and heat treatments in the area of the musculo-skeletal system.

It should be understood that the specifically disclosed embodiments are exemplary in nature and not to be construed as limiting the scope of the invention, as set forth in the appended claims.

I claim:

1. A topical composition for the treatment of pain comprising by weight percent of the total weight of the composition:
   a) about 1% to about 70% of a salicylate-based compound;
   b) about 1% to about 70% acetone;
   c) about 1% to about 30% of an emollient; and
   d) about 10% to about 50% menthol.

2. The topical composition of claim 1, wherein the composition comprises:
   a) about 5% to about 30% of a salicylate-based compound; and
   b) about 20% to about 60% acetone.

3. The topical composition of claim 2, wherein the composition comprises:
   (a) about 5% to about 20% of a salicylate-based compound; and
   (b) about 15% to about 33% acetone.

4. The topical composition of claim 1, wherein the composition comprises about 20% to about 40% menthol.

5. The topical composition of claim 1, wherein the composition comprises alpha-pinene, beta-pinene, Eucalyptol, limonene, sabine, myrcene, menthene, alpha-phellandrene, linalool, isopulegol, junipene, alpha-terpinene, gamma-terpinene, camphene and water.

6. The topical composition of claim 1 wherein said salicylate-based compound is methyl-salicylate and said emollient is palm oil.

7. The topical composition of claim 1, wherein said composition comprises:
   a) about 15% to about 25% acetone;
   b) about 0.5% to about 10% palm oil;
   c) about 1% to about 3% alpha-pinene;
   d) about 0.1% to about 5% beta-pinene;
   e) about 0.3% to about 5% camphene;
   f) about 0.3% to about 5% gamma-terpinene;
   g) about 1.8% to about 5% limonene;
   h) about 1.5% to about 5% sabinene;
   i) about 0.4% to about 5% myrcene;
   j) about 0.04% to about 5% menthene;
   k) about 0.05% to about 5% alpha-phellandrene;
   l) about 0.02% to about 5% linalool;
   m) about 0.01% to about 5% isopulegol;
   n) about 0.09% to about 5% junipene;
   o) about 0.13% to about 5% alpha-terpinene;
   p) about 5.6% to about 2% Eucalyptol;
   q) about 15% to about 40% menthol;
   r) about 5% to about 30% methyl salicylate; and
   s) about 01.% to about 5% water.

8. The topical composition of claim 1, wherein said composition comprises:
   a) about 15% to about 35% acetone;
   b) about 0.5% to about 10% of an emollient;
   c) about 1% to about 30% alpha-pinene;
   d) about 0.1% to about 5% beta-pinene;
   e) about 0.1% to about 5% limonene;
   f) about 0.1% to about 5% sabinene;
   g) about 0.4% myrcene;
   h) about 1% to about 20% Eucalyptol;
   i) about 15% to about 40% menthol; and
   j) about 5% to about 30% methyl salicylate.

9. The topical composition of claim 1, wherein said composition comprises:
   a) about 15% to about 35% acetone;
   b) about 0.5% to about 10% of an emollient;
   c) about 1% to about 30% alpha-pinene;
   d) about 1% to about 20% Eucalyptol;
   e) about 15% to about 40% menthol; and
   f) about 5% to about 30% methyl salicylate.

10. The topical composition of claim 1, wherein said composition comprises:
    a) about 15% to about 35% acetone;
    b) about 0.5% to about 10% of an emollient;
    c) about 1% to about 30% alpha-pinene;
    d) about 15% to about 40% menthol; and
    e) about 5% to about 30% methyl salicylate.

11. The topical compositions of claim 1, wherein the acetone, salicylate-based compound and emollient are commercial grade.

12. The topical composition of claim 1, wherein the composition is in the form of a gel.

13. The topical composition of claim 1, wherein the composition is in the form of an ointment.

14. The topical composition of claim 1, wherein the composition is in the form of a cream.

15. The topical composition of claim 1, wherein the composition is in the form of a salve.

16. The topical composition of claim 1, wherein the composition is in the form of a lotion.

17. The topical composition of claim 1, wherein the composition is in the form of a spray.

18. The topical composition of claim 1, wherein the composition is in the form of an aerosol.

19. A topical composition for treating pain associated with cancer wherein the composition comprises the composition of claim 1.

20. A topical composition for treating neck pain comprising the composition of claim 1.

21. A topical composition for treating shoulder pain comprising the composition of claim 1.

22. A topical composition for treating back pain comprising the step of topically administering an effective amount of the composition of claim 1 to the area of said pain.

23. A topical composition for treating surgical pain comprising the composition of claim 1.

24. A topical composition for treating bone injury pain comprising the composition of claim 1.

25. A topical composition for treating arthritic pain comprising the composition of claim 1.

26. A topical composition for treating muscle pain comprising the composition of claim 1.

27. A topical composition for treating pain associated with traumatic injuries comprising the composition of claim 1.

28. A topical composition for treating pain associated with hematomas comprising the composition of claim 1.

29. A topical composition for treating pain associated with myositis comprising the composition of claim 1.

30. A topical composition for treating pain associated with lower back syndromes comprising the composition of claim 1.

31. A topical composition for treating pain associated with spinal stenosis comprising the composition of claim 1.

32. A topical composition for treating bone pain associated with cancer comprising the composition of claim 1.

33. A topical composition for treating pain associated with osteoprotic fractures of the lumbar spine comprising the composition of claim 1.

34. A topical composition for treating pain associated with traumatic bone fractures in a mammal comprising the step of topically administering an effective amount of the composition of claim 1 to the area of said pain.

35. A topical composition for treating pain associated with herniated nucleus pulposus comprising the composition of claim 1.

36. A topical composition for treating musculo-skeletal pain comprising the composition of claim 1.

37. A topical composition for treating pain associated with joint dislocations comprising the composition of claim 1.

38. A topical composition for treating pain associated with herniated intervertebral disc comprising the composition of claim 1.

39. A topical composition for treating pain associated with prolapsed intervertebral disc comprising the composition of claim 1.

40. A topical composition for treating pain associated with a ruptured disc comprising the composition of claim 1.

41. A topical composition for treating pain associated with whiplash injuries comprising the composition of claim 1.

42. A topical composition for treating pain associated with fibromyositis comprising the composition of claim 1.

43. A topical composition for treating pain associated with intercostal rib pain comprising the composition of claim 1.

44. A topical composition for treating pain associated with muscle tear comprising the composition of claim 1.

45. A topical composition for treating pain associated with tendonitis comprising the composition of claim 1.

46. A topical composition for treating pain associated with bursitis comprising the composition of claim 1.

47. A topical composition for treating pain associated with meniscal tears comprising the composition of claim 1.

48. A topical composition for treating pain associated with tendon tears comprising the composition of claim 1.

49. A topical composition for treating pain associated with bone spurs comprising the composition of claim 1.

50. A topical composition for treating pain associated with cervical muscle hyperactivity comprising the composition of claim 1.

51. A topical composition for treating pain associated with immobilized tissue comprising the composition of claim 1.

52. A topical composition for treating bone, joint or muscle pain in an elderly subject comprising the composition of claim 1.

53. A topical composition for treating pain associated with geriatric related problems comprising the composition of claim 1.

54. A topical composition for treating pain associated with sports related injuries comprising the composition of claim 1.

55. A topical composition for treating pain associated with temporal mandibular joint syndrome comprising the composition of claim 1.

56. A topical composition for treating pain associated with pre-surgical and post-surgical orthopedic procedures wherein the composition comprises the composition of claim 1.

57. A topical composition for treating pain associated with post-surgical orthopedic recovery comprising the composition of claim 1.

58. A topical composition for treating pain associated with tendon, muscle, or bone repair comprising the composition or claim 1.

59. A topical composition for treating pain associated with joint replacement wherein said composition comprises the composition of claim 1.

60. A method for treating pain in a mammal comprising the step of topically administrating an effective amount of the composition of claim 1 to the area of said pain.

61. The method of claim 60, wherein the method is used in combination with physical therapy.

62. The method of claim 60, wherein the method is used in combination with electrical neuromuscular stimulation.

63. The method of claim 60, wherein the method is used in combination with an anesthetic.

64. The method of claim 60, wherein the method is used in combination with an oral analgesic.

65. The method of claim 60, wherein the method is used in combination with an oral anti-inflammatory.

66. The method of claim 60, wherein the method is used in combination with heat treatment.

67. The method of claim 60, wherein the method is used in combination with morphine-like agents.

68. The method of claim 60, wherein the method is used in combination with biofeedback techniques.

69. The method of claim 60, wherein the method is used in combination with acupuncture.

70. The method of claim 60, wherein the method is used in combination with cancer chemotherapy or radiation therapy treatments.

71. The method of claim 60, wherein the method is used in combination with sports related injury therapy.

72. The method of claim 60, further comprising the steps of:
   a) applying an effective amount of the present composition on the exact location or area around the location of the pain; and
   b) massaging the present composition on the skin.

73. The method of claim 60, wherein the composition is applied up to five times a day.

74. The method of claim 60, further comprising the following steps:
   a) diluting one part of the composition to five parts hot water in a bath; and
   b) soaking the pain affected area in the bath.

75. The method of claim 60, further comprising the following steps:
   a) applying the hot compress to the area of pain; and
   b) applying pressure to the hot compress while said compress is placed on the area of pain.

76. The method of claim 60, further comprising the following steps:
   a) diluting one part of the composition to five parts hot water in a whirlpool bath; and
   b) soaking a pain affected area in the bath, such that the motion of the water facilitates penetration of said composition through the mammal's skin.

* * * * *

UNITED STATES PATENT AND TRADEMARK OFFICE
CERTIFICATE OF CORRECTION

PATENT NO.    : 6,528,076 B2
DATED         : March 4, 2003
INVENTOR(S)   : Robert Small It is certified that error appears in the above-identified patent and that said Letters Patent is hereby corrected as shown below:

Column 1,
Line 64, "aloxipirin" should read -- aloxiprin --

Column 2,
Line 46, "arachidic" should read -- arachidonic --

Column 3,
Line 64, "0.09% and 0.13%" should read -- 0.09%, 0.09% and 0.13% --

Column 5,
Line 2, "methane" should read -- menthene --
Line 55, "carboxyl" should read -- carboxy --
Lines 57-58, "carboxyl methyl cellulose" should read -- carboxymethylcellulose --

Column 7,
Line 28, "osteoprotic" should read -- osteoporotic --
Lines 49- 50, "intervetebral" should read -- intervertebral --
Line 50, "intervetebral" should read -- intervertebral --

Column 9,
Line 20, "oxy-cotcontin" should read - oxycontin --
Line 20, "Demorol" should read -- Demerol --

Column 10,
Table 5, "5.6" should read -- 5.6% --
Table 5, "33.0" should read -- 33.0% --
Table 5, "8.6" should read -- 8.6% --

Column 11,
Line 46, "case" should read -- cases --

Column 14,
Line 18, "Osteoprotic" should read -- Osteoporotic --
Line 21, "osteoprotic" should read -- osteoporotic --

UNITED STATES PATENT AND TRADEMARK OFFICE
CERTIFICATE OF CORRECTION

PATENT NO.    : 6,528,076 B2
DATED         : March 4, 2003
INVENTOR(S)   : Robert Small It is certified that error appears in the above-identified patent and that said Letters Patent is hereby corrected as shown below:

<u>Column 15,</u>
Line 62, "sabine" should read -- sabinene --

<u>Column 16,</u>
Line 5, "3%" should read -- 30% --

<u>Column 17,</u>
Line 15, delete "the step of topically administering an effective amount of"
Lines 42-43, delete "the step of topically administering an effective amount of"
Line 53, "intervetebral" should read -- intervertebral --
Line 56, "intervetebral" should read -- intervertebral --

<u>Column 20,</u>
Line 3, "hot compress to the area" should read -- hot compress comprising the composition to the area --

Signed and Sealed this

Twenty-ninth Day of July, 2003

JAMES E. ROGAN
*Director of the United States Patent and Trademark Office*